United States Patent [19]

Ishizaki

[11] Patent Number: 5,026,641

[45] Date of Patent: Jun. 25, 1991

[54] BACTERIA CULTURE AND FERMENTATION USING THE SAME

[75] Inventor: Ayaaki Ishizaki, Fukuoka, Japan

[73] Assignees: The Yokohama Rubber Co., Ltd.; The Board of The Rubber Research Institute of Malaysia, both of Japan

[21] Appl. No.: 314,842

[22] Filed: Feb. 24, 1989

[30] Foreign Application Priority Data

Feb. 25, 1988 [JP] Japan .................. 63-43140

[51] Int. Cl.⁵ .......................... C12N 1/00; C12N 1/38; C12P 1/00; C12P 19/14

[52] U.S. Cl. .................................. 435/101; 435/100; 435/99; 435/253.6; 435/41; 435/243; 435/244; 435/252.1; 435/253.4; 435/255; 435/205; 435/200; 528/931; 528/932; 528/934; 528/936

[58] Field of Search ............... 435/99, 100, 101, 41, 435/243, 244, 252.1, 253.4, 255, 253.6; 528/931, 932, 934, 936

[56] References Cited

U.S. PATENT DOCUMENTS

| | | | |
|---|---|---|---|
| 1,259,794 | 3/1918 | Slocum | 528/932 |
| 2,097,481 | 11/1937 | Wallerstein | 528/932 |
| 4,338,399 | 7/1982 | Weil et al. | 435/99 |

*Primary Examiner*—Johnnie R. Brown
*Assistant Examiner*—Pamela S. Webber
*Attorney, Agent, or Firm*—Finnegan, Henderson, Farabow, Garrett & Dunner

[57] ABSTRACT

A process for culturing bacteria is disclosed in which is utilized as a bacterial nutrition a serum byproduced upon treatment of a natural rubber latex. The serum has an ample supply, a low cost, a stable quality and a sufficient activity over a wide variety of bacteria, thus contributing to accelerative growth for aerobic and anaerobic bacteria.

9 Claims, No Drawings

BACTERIA CULTURE AND FERMENTATION USING THE SAME

TECHNICAL FIELD

This invention relates to a process suitable for culturing bacteria and further to a process for the production of fermentation products employing such bacterial culture. The invention has a special concern with the use of serums resulting from treatment of natural rubber latexes.

BACKGROUND ART

By the serum is meant an aqueous solution byproduced upon coagulation and removal of a rubber component from a natural rubber latex. Serums have in most instances been disposed as wastes with the result that countries and territories of rubber tree cultivation are involved in environmental pollution problems.

However, such serums are thought to provide a good source of bacterial nutrition and hence a vast biomass as they are composed of proteins, organic acids, saccharides and derivatives thereof. Limited application of the serum has been found as a rubber additive as disclosed in Japanese Patent Publication No. 63-161002.

Bacteria have been allowed to grow, in the micrological industry, with the supply of various nutrition elements typified by amino acids, vitamines, minerals and the like and taken alone or in combination. In general, naturally occuring nutritions such as organic nitrogen are used to attain multinutrient cultures for bacteria. These nutrition elements are selected usually from a great number of materials including yeast extracts, polypeptones, meat extracts, defatted soybeans, defatted soybean hydrolyzates (HVP), corn steep liquors (CSL), cotton seed meals, peanut meals, pharmamedia, distillers solubles, livestock bloods, butchery wastes, casein hydrolyzates and the like.

Nutrition elements for use in culture media in commercial fermentation are required to be low in cost, abundant in supply without seasonal irregularities, stable in quality and effective for a wide variety of bacteria. Those meeting such requirements are limited only to HVP, CSL and yeast extract among the above listed nutrition elements. Because of their source of supply from byproducts in the food industry, however, HVP and CSL have posed an extreme shortage and a high price as a result of the changeover of processing methods in that industry. Yeast extract literally costs too high to warrant commercial acceptance.

DISCLOSURE OF THE INVENTION

Through extensive research efforts in which serums byproduced from natural rubber plants in Southeast Asia have been examined for their ability to grow numerous bacteria, it has now been found that bacterial growth can greatly be accelerated by the use of such otherwise undersirable serums either in particulate or liquid form. This is taken to mean that the serum has a high content of nutrition elements for bacteria.

With the foregoing difficulties of the prior art in view, the present invention seeks to provide a novel process for culturing bacteria which utilizers serums remaining as wastes after treatment of natural rubber latexes and thus enables a wide variety of bacteria to grow with utmost efficiency and at high yield with an ample supply of nutrition elements of lost cost and stable quality. The invention further provides a novel process for producing fermentation products with the use of such bacterial culture.

According to one aspect of the invention, there is provided with a process for culturing bacteria, which comprises the steps of preparing a culture containing a serum component, an enzymatically decomposed product thereof or a combination thereof, the serum component resulting from coagulation and removal of a rubber component from a natural rubber latex, and of fermenting and growing a bacterium in the culture.

According to another aspect of the invention, there is provided a process for producing fermentation products, which comprises the steps of preparing a culture containing a serum component, an enzymatically decomposed product thereof or a combination thereof, the serum component resulting from coagulation and removal of a rubber component from a natural rubber latex, and of fermenting and growing a bacterium in the culture, thereby producing a fermentation product.

BEST MODE OF THE INVENTION

In culturing bacteria and also in producing fermentation products, the present invention is characterized by the addition of a natural rubber latex serum and/or its enzymatically decomposed product as at least part of given culture media.

Serums eligible for the purpose of the invention are those derivable from removal of all of rubber components by acid coagulation from natural rubber latexes. This coagulation is effected in known manner using fumaric, acetic or sulfuric acid or the like.

An example of the composition of a fresh field rubber latex is tabulated below.

| Component | Content on latex basis (%) | Content on dry basis (%) |
| --- | --- | --- |
| rubber hydrocarbon | 35.62 | 88.28 |
| protein | 2.03 | 5.04 |
| acetone soluble (fatty acid) | 1.65 | 4.10 |
| saccharide | 0.34 | 0.84 |
| ash | 0.70 | 1.74 |
| water | 59.66 | 0 |

Industrially collected serums are liable to vary in composition with the nature of rubber latexes used and hence are difficult to define with accuracy. Contained in such a serum are about 50% of crude proteins plus nitrogen compounds, about 30% of saccharides, about 15% of ashes, i.e. inorganic salts such as of K, Mg, Cu, Fe, Na, Ca, P and the like, about 5% of water and traces of other components. Fatty and fibrous matters are found substantially null.

The rubber latex serum is obtained usually in too low a solids content of about 2 to 5% by weight and therefore may in practice be concentrated, as by evaporation, centrifuge or filtration, to a solids content of about 25 to 80% by weight.

In addition to the above serum of a solution form, a particulate form may suitably be used which is obtained by drying a starting serum of about 2 to 80% by weight in solids content so that transport and storage qualities are improved. With control, economy and efficiency in view, it is particularly preferred that a serum of 15 to 80% by weight in solids content be dried into particles of a predetermined particle size.

More specifically, a given serum is spray-dried into a drying chamber maintained at 150° to 250° C. in which sprayed droplets are instantaneously evaporated dry. Spray drying of a closed system may be employed to this end in which upon mechanical spraying of the serum, the droplets are brought into direct contact with hot air and dried into particles. This system of drying may be effected by the use of a nozzle type drier with a pressure nozzle or a two-fluid nozzle, or a disc type drier with a disc rotating axially at high speed. Disc type drying is particularly preferred. Nozzle pressures and disc speeds should preferably be in the range of 0.5 to 2.0 kg/cm$^2$ and in the range of 10,000 to 30,000 rpm, respectively. Desired serum components of 10 to 100 microns in particle size are dominated by the above specified ranges of pressures and speeds. Smaller particle sizes would render the resulting component hygroscopic and hence recoagulable, leading to deposits on the inner wall of the spray drier and also to massive products, which would in turn invite low yield. Greater particle sizes would fail to dissolve the finished component in water or solvent, causing objectionable bulkiness and inconvenient handling.

The drying chamber should preferably be maintained at a temperature lower than 130° C. with an inlet temperature of 150° to 250° C. and an outlet temperature of 50° to 130° C. In vacuo drying may be employed if necessary.

Importantly, the invention is contemplated to use the latex serum as it is or as previously hydrolyzed in the presence of a proteolytic enzyme such as protease or a microbial enzyme. Hydrolysis may be accomplished for example by admixing the serum with a proteolytic enzyme at a pH held on a certain level and with insoluble matter left unremoved.

No particular restriction is imposed upon the kind of cultures within which to incorporate the serum and/or its enzymatically decomposed product according to the invention. Liquid, solid and semi-solid cultures may suitably be applied as commonly used for bacterial fermentation. Such serum or decomposition product should preferably be used to partly or wholly replace the organic nitrogen contained in the culture.

Elemental analysis of the particulate serum component according to the invention is shown below.

| | |
|---|---|
| C | 22.0% |
| H | 5.5% |
| N | 9.5% |
| ash | 18.5% |

Taking the balance of organic nitrogen in view, the serum component is made up of 6% of insoluble nitrogen compounds, 1.5% of insoluble non-nitrogen compound, 16.5% of soluble nitrogen compounds, 28% of soluble non-nitrogen compounds, 28% of ammonium sulfate, 18% of ashes and 2% of moisture. Contained in the soluble non-nitrogen compounds are limited amounts of organic acids and reducing sugars which serve to act as fermenting materials. Thus, the serum component is thought to be not simply a carbon source nor an organic nitrogen source for fermentation.

The latex serum according to the invention has been found highly effective, in liquid or powdery form, in accelerating the growth of a wide variety of bacteria and yeasts. The serum can therefore be utilized as a substitute for yeast extract, HVP, CSL and the like in common use. The serum or its decomposition product is applicable equally to both aerobic and anerobic bacteria. Protease hydrolysis or unhydrolysis of the serum produces similar results on a selected class of bacteria.

The beneficial effects achieved by the use of the serum according to the invention are believed attributable not only to proteins and their decomposition products, amino acids, but also to synergistic combinations of the proteins with unidentified materials present in the serum.

EXAMPLES

The following examples are given to further illustrate the present invention, but should not be construed as limiting the invention. All natural rubber serums are referred to simply as "NRS".

EXAMPLE 1

A mixture of 10 g of glucose, 34 mg of MgSO$_4$.7H$_2$O, 77 mg of NaH$_2$PO$_4$.12H$_2$O and 10 mg of KCl was added with a proteolysis-induced NRS solution in an amount of 2 g on a dry NRS basis, followed by adjustment to pH 7.0 and dilution to a volume of one liter with pure water, thereby giving a test culture according to the invention. The NRS solution was prepared by taking 20 g of particulate NRS into one liter of a phosphorus buffer of 1/30 in mol and 7.0 in pH and by adding 200 mg of protease to the admixture, after which the resulting mixture was reacted at 30° C. for 12 hours. The solution showed a proteolysis ratio of 94%.

COMPARATIVE EXAMPLE 1

The procedure of Example 1 was followed except that 5 g of yeast extract (Oriental Yeast Co.) and 5 g of polypeptone (Daigo Nutrient Co.) were used in place of the NRS solution.

The cultures provided above were inoculated with 20 ml of *Streptococcus lactis* (ATCC, 19435) and then disposed to culture at 30° C. The bacterium used had been precultured overnight at 30° C. in a thioglyoxylate culture (TGC).

After a lapse of 12 hours, the bacterium weight was measured by the dry weighting method and the lactic acid yield by HPLC with the results shown in Table 1. The culture medium according to the invention has been confirmed satisfactory in respect of both microbial characteristics tested.

EXAMPLE 2

To an enzymatically saccharified solution of Casaba starch in an amount equivalent to 10 g of glucose were added 0.3 g of NRS (without protease treatment) and 0.5 g of peptone. The mixture after being adjusted in its pH to 6.2 was diluted with 100 ml of pure water. There was provided an inventive culture. The Casaba starch solution was prepared by dissolving 100 g of such starch in 500 ml of pure water and by adding to the solution 600 mg of alpha-amylase and maintaining the admixture at 70° C. for 30 minutes, followed by cooling at 40° C. and by subsequent reaction for 24 hours with addition of glucoamylase and with gentle shaking.

COMPARATIVE EXAMPLE 2

The procedure of Example 2 was followed except that 0.3 of yeast extract was used in place of NRS.

COMPARATIVE EXAMPLE 3

The procedure of Comparative Example 2 was followed except that yeast extract was omitted.

COMPARATIVE EXAMPLE 4

The procedure of Comparative Example 2 was followed except that neither yeast extract nor peptone was used.

Each of the four different cultures thus obtained was put into a meissel which was then sterilized. The culture was inoculated with 5 ml of *Zymomonas mobilis* (NRRL, B14023) and subjected to culturing for 2 days. The bacterium had been precultured in a liquid YM culture (Difco Co.) at 30° C. for 2 days. Measurement was made of the weight of the bacterium and the amount of ethanol that had been formed with the results given in Table 2.

As appears clear from the tabulated data, peptone as an additive, Comparative Example 3, has revealed inadequate bacterial growth. The use of the saccharified solution alone, Comparative Example 4, failed to give bacterial growth and ethanol formation.

EXAMPLE 3

The procedure of Example 2 was followed in preparing an inventive culture.

COMPARATIVE EXAMPLE 5

The procedure of Example 3 was followed except that 0.3 g of yeast extract and 0.3 g of malt extract were used in place of NRS.

COMPARATIVE EXAMPLE 6

The procedure of Comparative Example 5 was followed except that yeast and malt extracts were omitted.

COMPARATIVE EXAMPLE 7

The procedure of Comparative Example 5 was followed except that only the saccharified solution was used.

Bacterial growth and ethanol formation were examined under the conditions shown in Example 2 with the exception that the bacterium tested was *Saccharomyces urarum* (IFO 0565) precultured in a culture medium composed of 10 g of glucose, 3 g of yeast extract, 3 g of malt extract and 5 g of peptone, each such amount being based on one liter of the total medium and that inoculation was done in an amount of 5 liters.

Comparative Examples 6 and 7 were unaccetable with respect to the microbial qualities as is apparent from Table 3.

EXAMPLE 4 AND COMPARATIVE EXAMPLES 8 to 10

A basic culture medium was used in which were contained 1.0% of glucose, 0.07% of urea, 0.17% of sodium hexamethaphosphate, 0.1% of KCl and 0.04% of $MgSO_4.7H_2O$. The pH of the medium was 7.0. Four different cultures were prepared as formulated below.
 (1) 0.25% of particulate NRS added (Example 4)
 (2) no additive (Comparative Example 8)
 (3) HVP added to a concentration of 0.5 ml/dl (Comparative Example 9)
 (4) 0.25% of yeast extract added (Comparative Example 10)

A 20-ml fraction of each of the test cultures was put into a 500-ml shaking flask which was then sterilized. Inoculation was effected with *Pseudomonas aeruginosa* KYU-1 (FERM P-9701) precultured in a culture medium made up of 1.0% of glucose, 1.0% of yeast extract, 1.0% of polypeptone and 0.5% of NaCl and having a pH of 7.0. 100 microliters of a liquid culture was thereafter added which was obtained by shaking culture overnight at 30° C., followed by shaking culture at 30° C. for 3 days. Bacterial growth was determined with the results shown in Table 4.

The inventive culture is capable of acceleratively growing the bacterium. The control, Comparative Example 8, was not effective for such activity.

EXAMPLE 5

Liquid NRS was incorporated in a concentration of 1.0 ml/dl into a culture medium composed of 10% glucose, 0.1% of $KH_2PO_4$, 0.04% of $MgSO_4.7H_2O$, 0.001% of $FeSO_4.7H_2O$, 0.001% of $MnSO_4.4H_2O$, 100 gamma/liter of vitamine B1 and 3 gamma/liter of biotin. After being adjusted in its pH to 7.0, the mixture was sterilized and charged in an amount of 300 ml into a 1-liter minijar fermenter.

COMPARATIVE EXAMPLE 11

The procedure of Example 5 was followed except that HVP was added in a concentration of 0.75 ml/dl in place of NRS.

Both jars were inoculated with *Brevibacterlium flavum* (ATCC, 14067) precultured in a culture medium containing 1.0% of glucose, 1.0% of yeast extract, 1.0% of polypeptone and 0.5% of NaCl and having a pH of 7.0, followed by addition of 15 ml of a cultured liquid resulting from shaking culture overnight at 30° C. Culture was accomplished by aeration with stirring at ½ vvm (vol/vol/min) and 1,200 rpm while the pH was being maintained at 7.5 with a feed of aqueous ammonia. After 30 hours elapsed, the inventive culture produced a deposit of glutamic acid in an amount of 48.2%, whereas the comparative culture showed such a deposit of 46.5%.

TABLE 1

|  | Example 1 | Comparative Example 1 |
|---|---|---|
| bacterium weight (g/liter) | 1.28 | 1.25 |
| lactic acid formation (g/liter) | 9.2 | 9.0 |

TABLE 2

|  | Example 2 | Comparative Examples 2 | 3 | 4 |
|---|---|---|---|---|
| bacterium weight (mg/ml) | 1.61 | 2.05 | 0.84 | — |
| ethanol formation (ml) | 5.01 | 5.22 | 3.85 | — |

TABLE 3

|  | Example 3 | Comparative Examples 5 | 6 | 7 |
|---|---|---|---|---|
| bacterium weight (mg/ml) | 4.0 | 4.90 | 0.64 | 0.33 |
| ethanol formation (ml) | 4.58 | 4.8 | 1.99 | 0.84 |

TABLE 4

|  | Example 4 | Comparative Examples | | |
|---|---|---|---|---|
|  |  | 8 | 9 | 10 |
| bacterium weight (mg/ml) | 3.1 | — | 2.3 | 2.9 |

What is claimed is:

1. A process for culturing bacteria, which comprises: preparing a culture medium containing a nutrient component selected from the group consisting of a natural rubber latex serum which results from the removal of rubber components by coagulation from a natural rubber latex, the product which results from the hydrolysis of said serum in the presence of a proteolytic or starch-saccharified enzyme and mixtures of said serum and said hydrolysis product; inoculating said culture medium with a bacterium selected from the group consisting of *Streptococcus lactis, Zymomonas mobilis, Saccharmyces urarum Pseudomonas aeruginosa* KYU-1 and *Brevibacterlium flavum*; and growing said bacterium in said culture medium.

2. The process of claim 1 wherein said nutrient component is a liquid or particulate material.

3. The process of claim 2, wherein said nutrient component is in particulate form and has been prepared by spray drying.

4. The process of claim 2 wherein said particulate nutrient component has a particle size in the range of 10 to 100 microns.

5. The process of claim 1 wherein said culture medium is a liquid, solid or semi-solid culture medium.

6. The process of claim 1 wherein said bacterium is an aerobic or anaerobic bacterium.

7. The process of claim 1 wherein said nutrient component partly or wholly provides the organic nitrogen in said culture medium.

8. The process of claim 1 wherein said nutrient component is formed by hydrolyzing said latex serum in admixture with a proteolytic enzyme prior to addition to said culture medium.

9. A fermentation process which comprises the steps of preparing a culture medium containing a nutrient component selected from the group consisting of a natural rubber latex serum which results from the removal of rubber components by coagulation from a natural rubber latex, the product which results from the hydrolysis of said serum in the presence of a proteolytic or starch-saccharified enzyme and mixtures of said serum and said hydrolysis product; inoculating said culture medium with a bacterium selected from the group consisting of *Streptococcus lactis, Zymomonas mobilis, Saccharomyces urarum, Pseudomonas aeruginosa KYU*-1 and *Brevibacterlium flavum*; growing said bacterium in said culture medium; and using said bacterium in the fermentation of a starch or a sugar to produce an alcohol or an acid.

* * * * *

UNITED STATES PATENT AND TRADEMARK OFFICE
CERTIFICATE OF CORRECTION

PATENT NO. : 5,026,641
DATED : June 25, 1991
INVENTOR(S) : Ayaaki Ishizaki

It is certified that error appears in the above-identified patent and that said Letters Patent is hereby corrected as shown below:

Title Page, Assignee, change "The Yokohama Rubber Co., Ltd., The Board of The Rubber Research Institute of Malaysia, both of Japan" to --The Yokohama Rubber Co., Ltd., Tokyo, Japan; The Board of The Rubber Research Institute of Malaysia, Kuala Lumpur, Malaysia--

Claim 1, column 7, lines 22, 23, 24, change "Streptococcus lactis, Zymomonas mobilis, Saccharmyces urarum Pseudomonas aernginosa KYU-1 and Brevibacterlium flavum" to --_Streptococcus lactis_, _Zymomonas mobilis_, _Saccharmyces urarum_, _Pseudomonas aeruginosa_ KYU-1 and _Brevibacterlium flavum_--

Claim 9, column 8, lines 25, 26, 27, change "Streptococcus lactis, Zymomonas mobilis, Saccharomyces urarum, Pseudomonas aeruginosa KYU-1 and Brevibacterlium flavum" to --_Streptococcus lactis_, _Zymomonas mobilis_, _Saccharomyces urarum_, _Pseudomonas aeruginosa_ KYU-1 and _Brevibacterlium flavum_--.

Signed and Sealed this

Seventeenth Day of November, 1992

Attest:

DOUGLAS B. COMER

Attesting Officer     Acting Commissioner of Patents and Trademarks